United States Patent
Benetti et al.

(10) Patent No.: US 6,736,774 B2
(45) Date of Patent: *May 18, 2004

(54) XYPHOID ACCESS FOR CARDIAC SURGICAL PROCEDURES

(75) Inventors: Federico J. Benetti, Rosario (AR); Charles S. Taylor, San Francisco, CA (US); Michael V. Morejohn, San Jose, CA (US)

(73) Assignee: Cardiothoracic Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/757,128

(22) Filed: Jan. 8, 2001

(65) Prior Publication Data

US 2001/0001389 A1 May 24, 2001

Related U.S. Application Data

(63) Continuation of application No. 09/071,757, filed on May 1, 1998, now Pat. No. 6,199,556.

(51) Int. Cl.⁷ ................................................. A61B 1/32
(52) U.S. Cl. ........................ 600/231; 600/201; 128/898
(58) Field of Search .............................. 600/231, 232, 600/184, 201; 606/198

(56) References Cited

U.S. PATENT DOCUMENTS

| | | | |
|---|---|---|---|
| 3,882,855 A | 5/1975 | Schulte et al. ................ 128/20 |
| 4,048,987 A | 9/1977 | Hurson ......................... 128/20 |
| 4,049,000 A | 9/1977 | Williams ..................... 128/276 |
| 4,226,228 A | 10/1980 | Shin et al. .................... 128/20 |
| 4,421,107 A | 12/1983 | Estes et al. ................... 128/20 |
| 4,434,791 A | 3/1984 | Darnell ........................ 128/20 |
| 4,492,229 A | 1/1985 | Grunwald .................... 128/303 |
| 4,627,421 A | 12/1986 | Symbas et al. ............... 128/20 |
| 4,702,230 A | 10/1987 | Pelta ............................ 128/20 |
| 4,726,356 A | 2/1988 | Santilli et al. ................ 128/20 |
| 4,852,552 A | 8/1989 | Chaux .......................... 128/20 |
| 4,865,019 A | 9/1989 | Phillips ........................ 128/20 |
| 4,949,707 A | 8/1990 | LeVahn et al. ............... 128/20 |
| 4,971,037 A | 11/1990 | Pelta ............................ 128/20 |
| 4,993,862 A | 2/1991 | Pelta ............................ 403/59 |
| 5,025,779 A | 6/1991 | Bugge ......................... 128/20 |

(List continued on next page.)

FOREIGN PATENT DOCUMENTS

| | | |
|---|---|---|
| EP | 0 803 228 A1 | 10/1997 |
| FR | 473451 | 1/1915 |
| GB | 168216 | 9/1921 |
| GB | 2 267 827 | 12/1993 |
| WO | WO 97/32514 A3 | 9/1997 |
| WO | WO 97/32514 A2 | 9/1997 |
| WO | WO 99/09892 | 3/1999 |
| WO | WO 00/10466 | 3/2000 |

OTHER PUBLICATIONS

Ancalmo, N.and J. L. Ochsner: "*A Modified Sternal Retractor*," Ann. Thorac, Surg. 21 (1976) 174.

(List continued on next page.)

*Primary Examiner*—David H. Willse
*Assistant Examiner*—Javier G. Blanco
(74) *Attorney, Agent, or Firm*—Law Office of Alan W.C.

(57) ABSTRACT

Surgical procedures on the beating heart are enabled by an incision made in the xyphoid area and specially designed retractors and related devices to facilitate cardiac surgical procedures. Specifically, coronary artery bypass graft procedures (CABG) are achieved using a vertically offsetting retractor or access platform in combination with a beating heart stabilizer. The surgical methodology permits procedures such as the CABG procedure without penetrating the rib cage or performing a sternotomy or thoracotomy.

13 Claims, 7 Drawing Sheets

U.S. PATENT DOCUMENTS

| | | | |
|---|---|---|---|
| 5,052,373 A | 10/1991 | Michelson | 128/20 |
| 5,080,088 A | 1/1992 | LeVahn | 128/20 |
| 5,159,921 A | 11/1992 | Hoover | 128/20 |
| RE34,150 E | 12/1992 | Santilli, deceased et al. | 128/20 |
| 5,306,234 A | 4/1994 | Johnson | |
| 5,520,610 A | 5/1996 | Giglio et al. | 600/233 |
| 5,727,569 A | 3/1998 | Benetti et al. | 128/898 |
| 5,730,757 A | 3/1998 | Benetti et al. | 606/198 |
| 5,772,583 A | 6/1998 | Wright et al. | 600/232 |
| 5,879,291 A | 3/1999 | Kolata et al. | 600/227 |
| 5,882,299 A | 3/1999 | Rastegar et al. | 600/232 |
| 5,908,382 A | 6/1999 | Koros et al. | 600/232 |
| 5,944,736 A | 8/1999 | Taylor et al. | 606/198 |
| 5,947,896 A | 9/1999 | Sherts et al. | 600/229 |
| 5,967,972 A | 10/1999 | Santilli et al. | 600/232 |
| 5,976,080 A | 11/1999 | Farascioni | 600/213 |
| 5,976,171 A | 11/1999 | Taylor | 606/198 |
| 5,984,867 A | 11/1999 | Deckman et al. | 600/232 |
| 6,036,641 A | 3/2000 | Taylor et al. | 600/231 |
| 6,199,556 B1 | 3/2001 | Benetti et al. | 128/898 |

OTHER PUBLICATIONS

Angelini, G.D., M.D. et al., "*A Fiber–Optic Retractor for Harvesting the Internal Mammary Artery*," Ann. Thorac. Surg. (1990; 50:314–5).

Antinori, C., et al., "*A Method of Retraction During Reoperative Coronary Operations Using the Favaloro Retractor*," The Society of Thoracic Surgeons: 1989.

Beg, R.A., "*Internal Mammary Retractor*," Ann Thorac, Surg. 39 (1985) 286–287.

Campalani, G., M.D., et al., "*A New Self–retaining Internal Mammary Artery Retractor*," J. Cardiovas. Surg. 28, 1987.

Chaux, A. and Blanche, C., "*A New Concept in Sternal Retraction: Applications for Internal Mammary Artery Dissection and Valve Replacement Surgery*," Ann. Thorac. Surg. 42 (1986) 473–474.

Delacroix–Chevalier Surgical Instruments, IMA Saving Packages Brochure.

Guzman, F. M.D. et al., "*Transient Radial Nerve Injury Related to the Use of A Self Retraining Retractor for Internal Mammary Artery Dissection*," J. Cardiovasc Surg. 30, 1989.

Itoh, Toshiaki, M.D., et al., "*New Modification of a Mammary Artery Retractor*," Ann. Thorac. Surg. 1994; 57:1670–1.

McKeown, P. P., et al., "*A Modified Sternal Retractor for Exposure of the Internal Mammary Artery*," Ann. Thorac. Surg. 32 (1981) 619.

Phillips, S. J., M.D. et al., "*Versatile Retractor for Use in Harvesting the Internal Mammary Artery and Performing Standard Cardiac Operations*," J. Thorac. Cardiovasc. Surg. (1989; 97:633–5).

Pilling Surgical Instruments, A Rusch International Company Brochure.

Pittman, J, M.D., et al., "*Improved Visualization of the Internal Mammary Artery with a New Retractor System*," Ann. Thorac. Surg., 1989; 48:869–70.

Roux, D., M.D., et al., "*Internal mammary Artery Dissection: A Three Dimensional Sternal Retractor*," J. Cardiovasc. Surg., 1989; 30:996–7.

USSC Cardiovascular Thora–Lift J, United States Surgical Corporation, Norwalk, Connecticut, Product Brochure.

Vincent, J.G., "*A Compact Single Post Internal Mammary Artery Dissection Retractor*," Eur. J. Cardio–Thor. Surg. 3 (1989) 276–277.

XYPHOID ACCESS FOR CARDIAC SURGICAL PROCEDURES

RELATED APPLICATIONS

This application is continuation of application Ser. No. 09/071,757 filed on May 1, 1998 which issued on Mar. 13, 2001 as U.S. Pat. No. 6,199,556.

FIELD

The field of the invention is specially designed instruments and methods for cardiac surgery using a transxyphoid incision.

BACKGROUND

Prior techniques to reduce the trauma and expense of cardiac surgery include closed chest procedures using specially configured catheter-based apparatus to achieve cardiopulmonary bypass (CPB) combined with less invasive port-access type incision and special techniques and apparatus to eliminate CPB by employing a minimally invasive surgical technique and performance at the surgical procedure on the beating heart. These existing closed chest procedures eliminate the trauma associated with an open chest incision but still have the drawbacks associated with CPB. The existing beating heart procedures avoid CPB but still typically require a transthoracic incision, i.e., an incision that penetrates the rib cage in some fashion. Thus, while these approaches provide a less invasive procedure compared to the traditional medial sternotomy or thoracotomy, any procedure that traverses the ribs or sternum may cause complications and may slow the post-operative recovery of the patient.

SUMMARY OF THE INVENTION

The several inventions described here are devices and methods to facilitate minimally invasive cardiac surgery on the beating heart using an incision in the xyphoid region to provide access to the beating heart. The methodology of the invention enables a beating heart coronary artery bypass graft (CABG) procedure without a port-access or other incision that penetrates the rib cage. The use of a surgical retractor to spread the ribs apart from one another is avoided thus the possibility of broken ribs and the possible necessity of remaining portions of ribs is eliminated.

Moreover, typically the pleura remains intact, a result that speeds recovery and guards potential complications. The devices of the incision are specially designed to facilitate the xyphoid incision approach and avoid CPB by enabling the surgery to be performed on the beating heart. The devices of the invention include, individually and in combination, a specialized retractor to facilitate access to the beating heart through the xyphoid incision, or beating-heart stabilizer, and other complementary surgical instruments.

Specifically, the invention includes a retractor or access platform designed to provide the function of a vertical offset of the lower sternum and preferably further comprising attachments to affix complementary surgical instruments, including at least a stabilizer for the beating heart. Generally, the stabilizers are of the type disclosed in PCT Application US 96/15091 (WO/10753), EPO Application 97/02789.1, and U.S. Pat. No. 5,727,569. The specially designed retractors described herein may also incorporate lights, blowers, suction or other conventional apparatus to facilitate surgical procedure.

DETAILED DESCRIPTION OF THE INVENTION

A preferred surgical procedure to access the beating heart via a xyphoid incision is described as follows. The term "xyphoid incision" refers to a surgical incision proximate to, but not necessarily directly above, the xyphoid appendage. The xyphoid incision of the invention provides a surgical field and access site to the heart that extends through an opening beneath the sternum and preferably immediately beneath the lowest rib. See also Full-Spectrum Cardiac Surgery Through a Minimal Incision: Mini-Sternotomy (Lower Half) Technique Doty et al. *Annals of Thoracic Surgery* 1998; 65(2): 573–7; Transxiphoid Approach Without Median Sternotomy for the Repair of Atrial Septal Defects, Barbero-Marcial et al. *Annals of Thoracic Surgery* 1998; 65(3): 771–4 which are specifically incorporated herein by reference.

Figure 1:
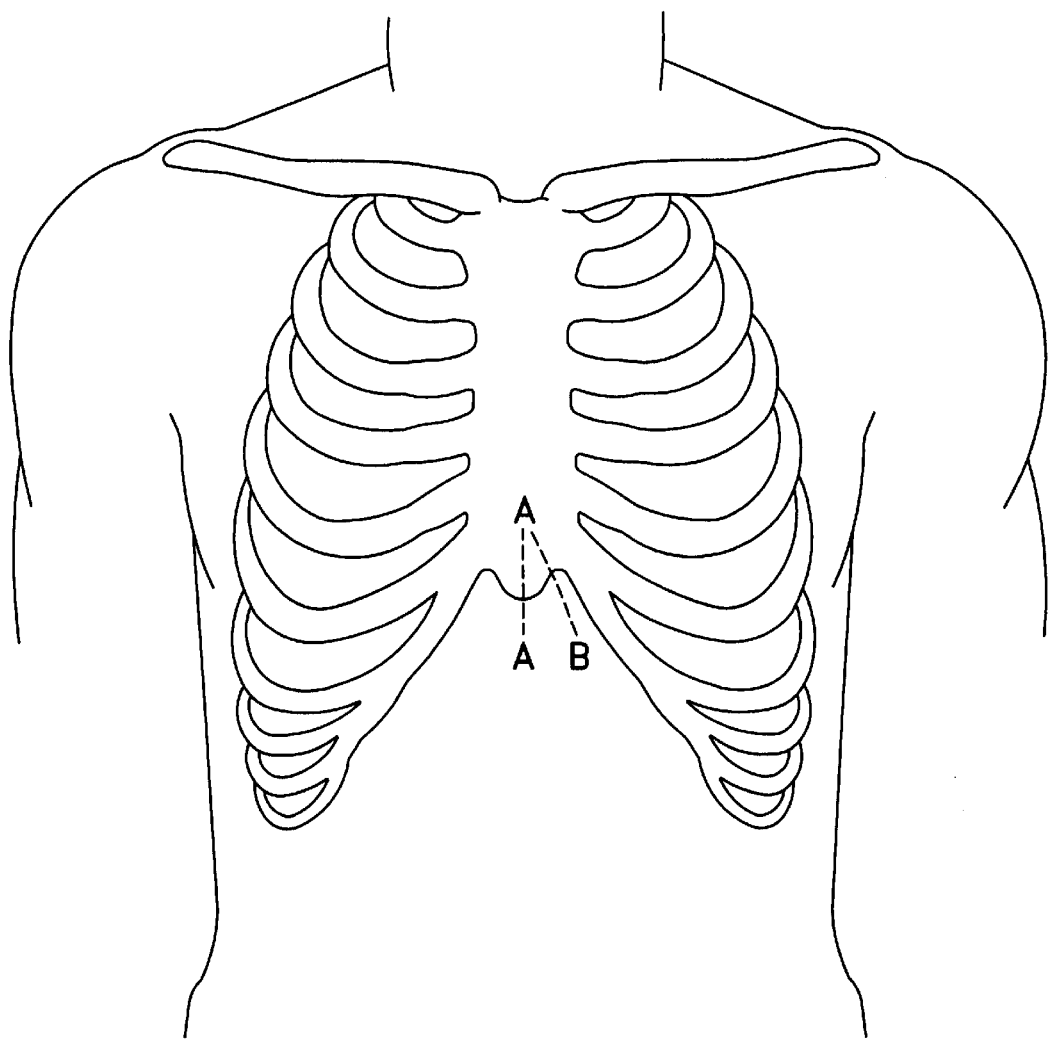
FIG. 1 is a general representation of the thoracic region of a patient showing the sternum rib cage, and the xyphoid appendage.

Deferring to FIG. 1, a vertical skin incision is made above the xyphoid process and the center of xyphoid appendage is transected. Because the xyphoid appendage is cartilagenous, the appendage need not be removed and the sternum need not be transected. The total length of the xyphoid incision depends on length of xyphoid appendage, i.e., longer xyphoids are less likely to require any cutting into the sternum. See also FIGS. 3, 5 and 6. The maximum incision should be approximately 6–7 cm from below the tip of the xyphoid appendage upwards towards the patient's head. The incision may be extended downward below the xyphoid appendage to the extent necessary to provide an adequate surgical field, but as noted above, the maximum length should not greatly exceed 6–7 cm. The incision may be strictly vertical or may be slightly curved, following the outline of the butt of either the right or left rib cage, depending on the selected coronary arteries to be accessed. In most cases, a curved incision will follow the lower left rib. An approximately 1 cm incision may be made in the pericardium to accommodate insertion of a surgical scope. The scope preferably has a flexible housing and at least a 16× magnification. Insertion of the scope through the pericardial incision allows the surgeon to analyze and "inventory" the coronary arteries and mammary arteries to plan the procedure depending on the clinical status of the individual patient. For example, the analysis may include determining the distance between the mammary arteries (left and/or right) and the coronary arteries to be bypassed to determine the necessary length of the mammary artery to be dissected from the vasculature. Visual inspection also reveals the functional and physical characteristics of the coronary and mammary arteries, i.e., the texture/color of the epicardium help to indicate the extent of the stenosis. Also, the position of the coronary arteries, including whether or not the target arteries are "intramyocardial" (below the surface of the epicardium), will indicate the access space (and volume) required at the surgical site and in the surgical field. At this point, the surgeon can confirm that a xyphoid access is appropriate for the particular procedure to be performed.

As described in more detail in the Figures and the following text, a vertically offsetting retractor or access platform is used to engage a portion of the rib cage capable of lifting at least one rib and preferably more than one rib and the sternum, see FIGS. 2–6. The term "offsetting" herein is used to describe a manipulation of at least one rib that provides access to the thoracic cavity via the xyphoid incision, generally described herein as "xyphoid access." Typically, the vertical offsetting procedure comprises engaging the lowermost rib with an offsetting retractor or access platform as disclosed herein and lifting at least a portion of the lowermost ribs. This may be accomplished by simultaneously applying force at one or more points about the chest and pelvis, and preferably includes at least a mechanical force applied to vertically to orient at least a portion of the lower region of the sternum and a rib cage relative to the remainder of the body below the rib cage. As noted, this orientation is most readily achieved by lifting one half of the lower edge of the rib cage, adjacent to the xyphoid appendage using a specially designed surgical retractor. Although retraction devices such as those described below and in U.S. Pat. No. 5,730,757 are preferred, other more conventional devices could be adapted, see for example U.S. Pat. No. 5,026,779; U.S. Pat. No. 4,726,358; U.S. Pat. No. 4,852,552; A New Concept in Sternal Retraction: Applications for Internal Mammary Artery Dissection and Valve Replacement, Chaux, et al. *Ann. Thor. Surg.* 42(1986) 473–474; A Modified Sternal Retractor, Ancalmo, et al. *Ann. Thorac. Surg.,* 21(1976)174; Internal Mammary Retractor, Beg et al. *Ann. Thorac. Surg.,* 39 (1985) 286–287; A Modified Sternal Retractor for Exposure of the Internal Mammy Artery, McKeown, et al. *Ann. Thorac. Surg.,* McKeown, et al. 32 (1981) 619; A Compact Single Post Internal Mammary Artery Dissection Retractor, Vincent, et al. *Eur. J. Cardio-Thor. Surg.,* 3 (1980) 276–277.

Collectively, these devices provide access to the beating heart via a xyphoid incision and comprise means for offset retraction of the lower rib cage. As shown in the Figures, the right or left lower rib cage may be vertically offset separately from the remainder of the rib cage, and the entire lower rib cage may be elevated relative to the upper rib cage separately, or in addition to, the displacement of either side.

In addition to the offsetting retractor, additional apparatus are preferred for use in a surgical procedure using xyphoid access. As noted above, a surgical scope may be used to evaluate the position and configuration of the source or target arteries of a coronary artery bypass. When the gastroepiploic artery is the source, direct view through the xyphoid incision may be adequate. However, for most procedures, a scope is preferred, especially for harvesting in an internal mammary artery (LIMA, RIMA) and for completion of the anastamosis. In least invasive procedures, the scope will be useful in forming the proximal anastaosis, particularly where a vein graft is used. As noted above, a stabilizer for beating heart surgery is also used. Devices for beating-heart stabilization are described in U.S. Pat. No. 5,727,569 and PCT Application US 96/15091 (WO/10753) wherein suction is used to attach the stabilizer to the beating heart, and EPO Application 97/02789.1 wherein a mechanical force is applied to the beating heart proximate to the site of a target coronary artery, which are specifically incorporated herein by reference.

Also because the size of the incision is preferably minimized in the procedures described herein, an organ or tissue positioner may advantageously be used to retract or reposition tissue or internal organs at the site of the incision or inside the thoracic cavity near the site of the surgery. The positioner or retractor may be of any conventional mechanical design, or expandable by inflation on manipulation, and is preferably suitable for minimally invasive procedures. Moreover, a tissue or organ positioner may be affixed to the offsetting retractor during the procedure to maintain access to the surgical field.

When performing a CABG procedure, the source artery is prepared as one of the initial steps. Typically, dissection of the distal end of an internal mammary (LIMA or RIMA) is performed. A non-hand held retractor may be used to avoid capturing or pinching the artery with the blade. After harvesting a mammary artery, or otherwise preparing the source artery, the offsetting retractor means may be replaced with a horizontally spreading retractor that may have a fixture attached for mounting a beating-heart stabilizer. Ideally, however, the same retractor has both offsetting and horizontal spreading capabilities, and an integral fixture for mounting the stabilizer. Beating-heart stabilizers having varying or variable lengths may be necessary, i.e., a stabilizer having a longer shaft may be necessary to reach the circumflex and diagonal arteries. The anastamotic connections are then made while employing the stabilizer to render the target coronary artery substantially motionless. A scope is used as necessary. When the anastamotic connections are completed, a small incision is made below the xyphoid appendage and a drainage tube is inserted into the pericardium, if the pleura has not been opened, and into the pluera itself if it has been opened. Before finally closing the xyphoid incision, a scope is used to check the anastomosis for kinking or bleeding, to check the position of the drainage tube, and to check the integrity of the pleura. A flow probe may also be inserted to check the patency of the anastamosis.

FIG. 1 illustrates a generic representation of the human thoracic cavity showing the orientation of the sternum, collarbone, and ribs. A xyphoid incision providing access to the beating heart as described above may be made along line A-A. Alternatively, where the incision is aligned along the edge of the lower rib cage, which is particularly preferred for access to the beating heart, the incision may be made along line A-B. As noted, above, the incision should be no longer than approximately 6–7 cm, but may vary depending on the condition of the patient, the orientation of the source and target coronary arteries for the anastomosis, and other conditions dictated by the clinical condition of the patient.

Figure 2:
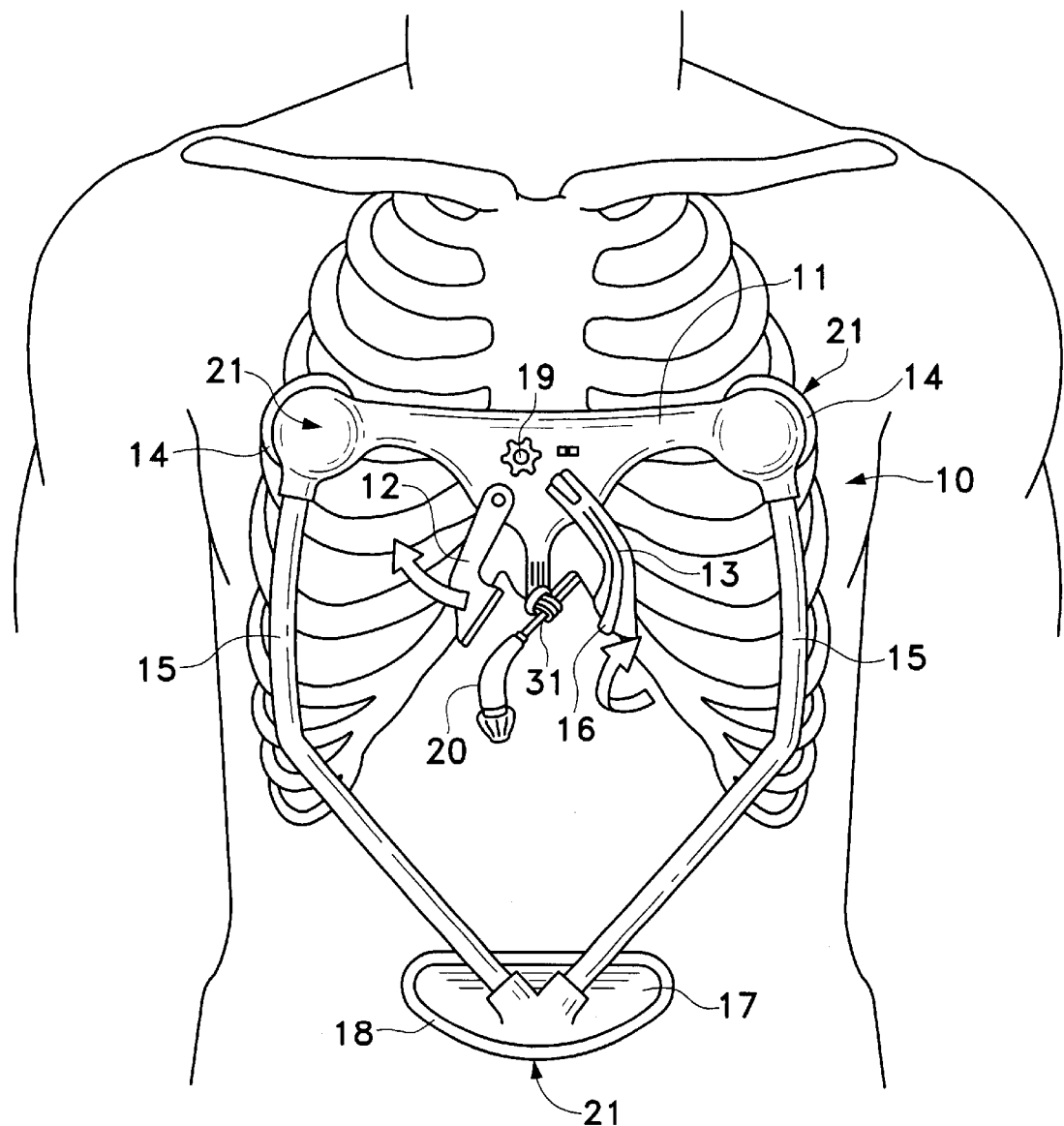
FIG. 2 is an embodiment of the offsetting retractor assembly of the invention shown in place on a surgical patient with a retractor assembly and associated apparatus to complete a surgical procedure via a xyphoid appendage.

Referring to FIG. 2, a retractor assembly or access platform 10 is provided that has the capability to vertically offset the lower portion of the rib cage. In one embodiment, the retractor assembly 10 is comprised of a retractor frame 11 which is preferably rigid as in a conventional retractor. In the embodiment shown in FIG. 2, the main body at the frame 11 serves as a mounting point for a retractor arm 12 and a lifting arm 13 which are attached to the frame preferably at a substantially central location relative to the contacts points described below at which the retractor assembly 10 contacts the body. To increase the stability of the frame 11, the frame has at least one support pad affixed to the lower portion of the frame 11 at each contact point 21 where the retractor assembly contacts the body. As shown in FIG. 2, contact points 21 are preferably positioned at the extremities of the frame 11 and are configured to rest against the chest or frontal body of the patient to provide maximum stability for the retractor assembly 10. In a preferred embodiment, the frame 11 of the retractor assembly 10 is further comprised of support arms 15 that extend away from the body of the frame 11. In embodiment where the retractor arm 12 and lifting arm 13 extend away from frame 11 towards to lowermost portion of the rib cage, the support arms 15 extend in like direction, preferably to a point beyond the position of the retractor arm 12 and lifting arm 13. Therefore, because the function of the support arms 15 is to act as a brace for the frame 11 and the retractor arm 12 and lifting arm 13, when part of a unitary device, the support arms 15 will preferably extend in the same direction away from the frame 11 as the retractor arm 12 and lifting arm 13. It will be apparent to those of ordinary skill that, in varying configurations, the retractor arms 12, lifting arm 13, frame 11, and support arms 15, each will be configured to maximize the stability of the retractor assembly 10. The support arms 15 may also be configured to engage or be affixed to a rigid support (not shown) such as an operating table or other fixed structure. Alternatively, for a unitary device, the support arms 15 are preferably connected to a contact point 21 that provides a retractor assembly brace 17. The retractor assembly brace 17 is located at a point to offset the force exerted on the frame 11 by the retractor arm 12 or lifting arm 13. Thus, in the embodiment of FIG. 2, the arms engage the rib cage at a point that is intermediate to the contact points 21. The retractor assembly brace 17 is preferably provided with a pressure pad 18 at the contract point 21 and on the bottom surface thereof, and that rests against the body of the patient at a point below the xyphoid. In a preferred configuration, the retractor assembly brace 17 and pressure pad 18 exert a force against the pubic bone to stabilize the retractor assembly 10 and to counter the force generated by the vertical offset function of the retractor assembly 10. For ease of assembly and disassembly, support arms 15 may snap into sockets on the frame 11 or on the retractor assembly brace 17. As will be readily apparent, the embodiment of FIG. 2, specifically the orientation of the frame 11, the support arms 15, and the retractor assembly brace 17, are designed to provide a stable platform such that the retractor arm 12 and the lifting arm 13 may be manipulated and positioned to provide a stable surgical field when a xyphoid access incision is used for minimally invasive surgery on a beating heart. To retract and offset the xyphoid access incision, the retractor arm 12 is inserted in the xyphoid incision to engage the lowermost edge of the lower rib. As in a conventional surgical retractor, the retractor arm 12 may have a spreader member 19 to move the retractor arm 12 to horizontally retract the tissue, bone or other structure engaged by the blade 20 of the retractor arm 12. The spreader member 19 may be a hand-crank, a cable and pulley assembly, or virtually any other mechanical expedient that is typically operated by hand to move the retractor arm 12. The lifting arm 13 preferably moves independently of the retractor arm 12, but may also be operably connected to a spreader member 19 to provide the offset retraction function. As will be described in more detail in the following embodiments, the retractor assembly 10 may also have associated therewith additional devices to facilitate the surgical procedure performed through the xyphoid incision. A fiber optic 16 light may be attached to the retractor arm 12, the lifting arm 13, the frame 11, or any other convenient point to provide lighting at the surgical field. Additionally, a beating-heart stabilizer 20 is integrally attached by being mounted on a portion of the frame 11, retractor arm 12, or lifting arm 13. The beating heart stabilizer 20 is attached to the frame by means of a dedicated fixture that is located at a point on the retractor assembly 10 that facilitates introducing the stabilizer 20 to the beating heart and fixing the stabilizer 20 in position once the requisite stabilization of the beating heart is achieved. As noted above, the lifting arm 13 provides for vertical offset retraction of a portion of the rib cage, preferably the left rib cage and most preferably the lowest left rib is vertically offset while the horizontal retraction is also provided in a single device that serves as a mount for the beating-heart stabilizer 20. However, these respective functions can be provided by two discrete retractor devices without departing from the spirit of the invention. The mechanical function of the lifting arm 13 is described detail below.

Figure 3:
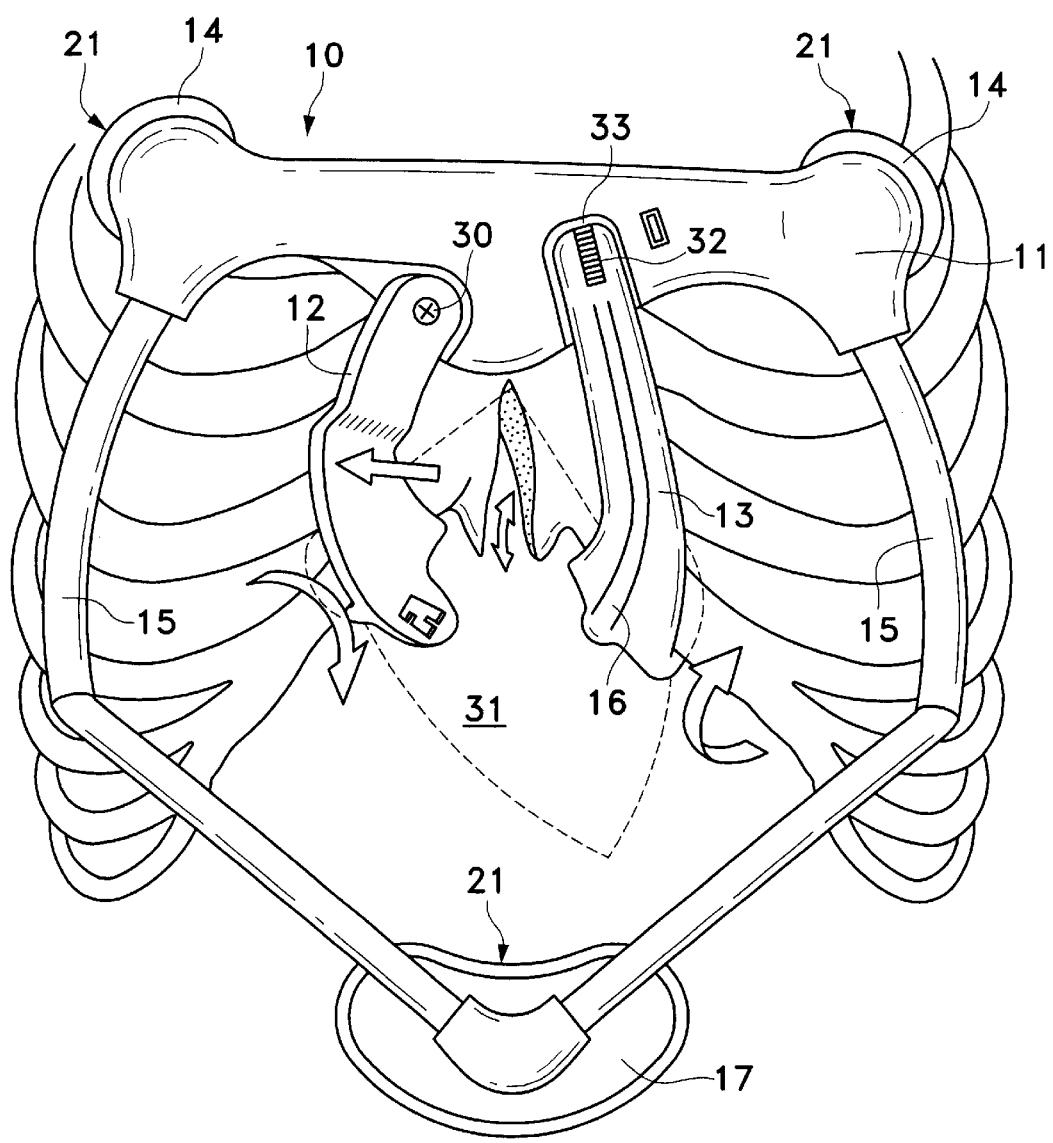
FIG. 3 is an embodiment of the offsetting retractor assembly of the invention with retracting and lifting arms engaged at the lower rib on the right and left side, respectively, of a patient.

Referring to the embodiment of FIG. 3, the retractor arm 12 may rotate around a hinge to increase the size of the xyphoid incision. The hinge 30 attaches the retractor arm 12 to the frame 11 at a convenient point and also provides the axis of rotation about which the retractor arm 12 may be positioned. As shown in FIG. 3, the xyphoid incision may bisect a cartilagenous portion of the xyphoid appendage; placement of the retractor arm 12 and lifting arm 13 adjacent to, and on either side of, the xyphoid maximizes the utility of the offset function, and provides an ideal surgical field. Also, in this configuration, a mounting fixture 31 for a beating heart stabilizer (not shown) is readily provided on the most distal portion of the retracting arm 12. The location and orientation of the mounting fixture 31 for the beating heart stabilizer mount is a matter of choice subject to facilitating minimally invasive insertion and removal of the stabilizer combined with advantageous positioning of the distal end of the stabilizer at the target coronary artery of the beating heart. See PCT Application US 96/15091 (WO/10753), EPO Application 97/02789.1, and U.S. Pat. No. 5,727,569. The vertical offset function is provided by the capacity of lifting arm 13 to be raised in a direction above and generally perpendicular to the horizontal lie of the patient. To maintain the surgical field created by the xyphoid access incision, the lifting arm 13 is fixed in place by a locking mechanism 32 that may be comprised of any mechanical expedient that fixedly maintains the lifting arm 13 in position. The embodiment of FIG. 3 shows a conventional lockable ratchet mechanism that fixes the lifting arm 13 in place at incremental positions of a vertically offset configuration relative to the position of the frame 11 and the retractor arm 12. As noted above and as shown in FIG. 3, the distal portion of the lifting arm 13 ideally engages the lower edge of the bottom rib at a point proximate to and below the xyphoid appendage to provide for maximum access and maximum stability when the lifting arm 13 is raised and fixed into position to provide access to the beating heart via the xyphoid incision. As noted above in connection with FIG. 2, the contact points 21 and support pads 14 are affixed to the frame 11 and, together with the retractor assembly brace 17, are spaced to provide overall stability for the retractor assembly 10 and ease of access for the surgeon. The positioning of the contact points 21, frame 11, and retractor assembly brace 17 is preferably in a substantially triangular or rectangular configuration, although a triangular configuration is preferred for distribution of force. Thus, the contact points 21 and retractor assembly brace 17 form at least three contact points where the retractor assembly 10 engages the body of the patient. The contact points 21 are oriented in a nonlinear orientation and to substantially surround the functional elements of the retractor, mainly the retractor arm 12 and the lifting arm 13, and the beating-heart stabilizer 20. As shown in FIGS. 2 and 3, the operative elements of the retractor assembly are contained within an imaginary triangle formed by connecting the locations of the contact points 21 comprising the support pads 14 and the retractor assembly brace 17.

Figure 4:
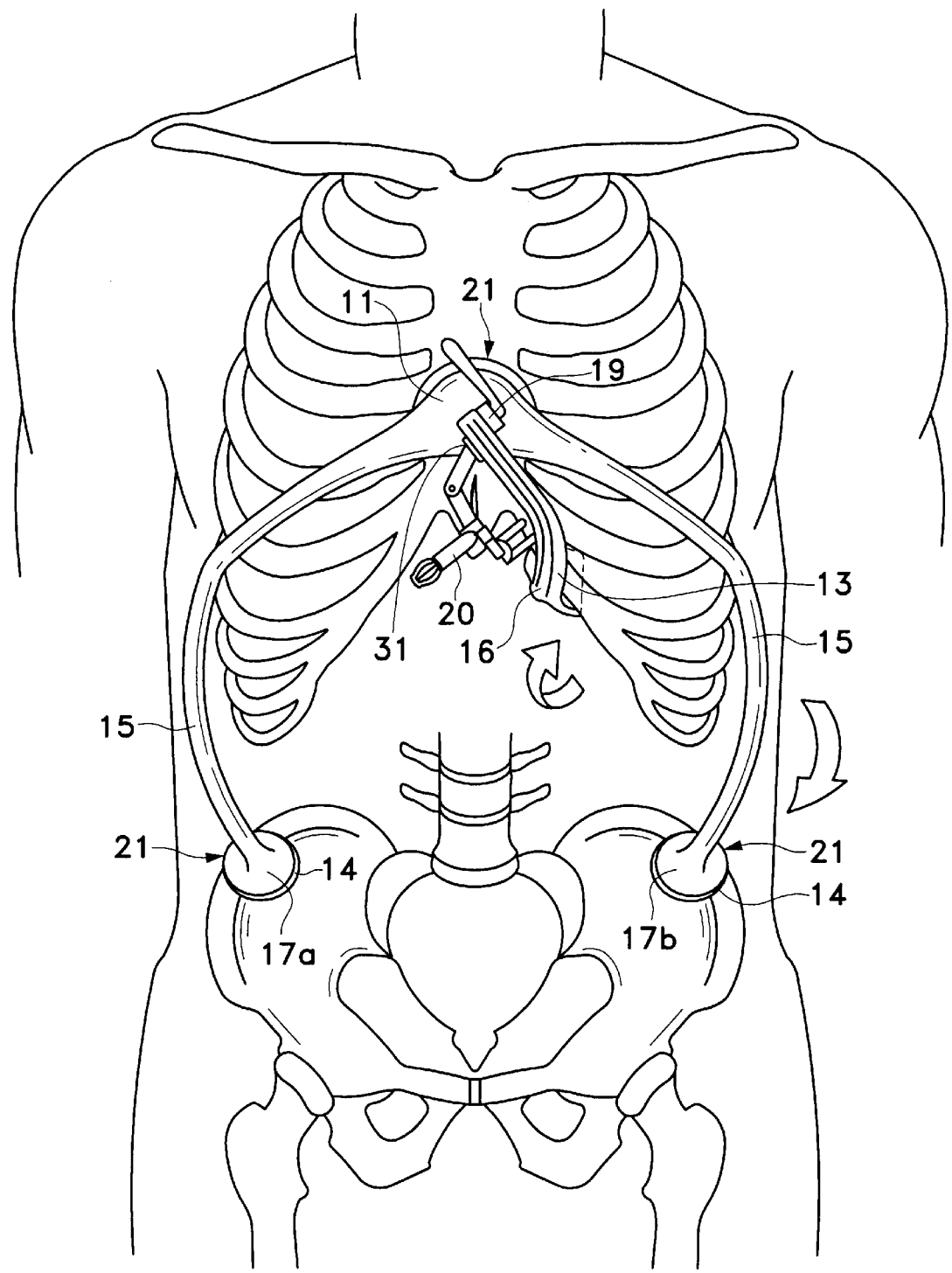
FIG. 4 is a side view of an embodiment of the offsetting retractor assembly of the invention showing a preferred placement of the assembly relative to the rib cage and pelvis of a patient.

FIG. 4 is an embodiment of a retractor assembly similar to the embodiment of FIGS. 2 and 3 wherein the retraction assembly 10 has an integral frame 11 with support arms 15 configured to provide three contact points 21. In this embodiment, one contact point 21 is positioned at an upper intermediate point of the frame 11, this point is preferably located such that the uppermost point of the frame 11 is rested against the center of the sternum of the patient, just above the xyphoid appendage. As can be seen in FIG. 4, a pair of retractor assembly braces 17a, 17b, are oriented to rest against both sides of the pelvis. This embodiment features only a single lifting arm 13 and no retractor arm is used. The spreader member 19 acts only upon the lifting arm 13 and serves to vertically offset the lifting arm 13 relative to the frame 11 when the spreader member 19 is actuated by hand. As in the embodiment of FIGS. 2 and 3, a beating-heart stabilizer mounting fixture 31 is provided, in the case located directly on the frame 11, for attachment of a beating heart stabilizer 20.

Figure 5:
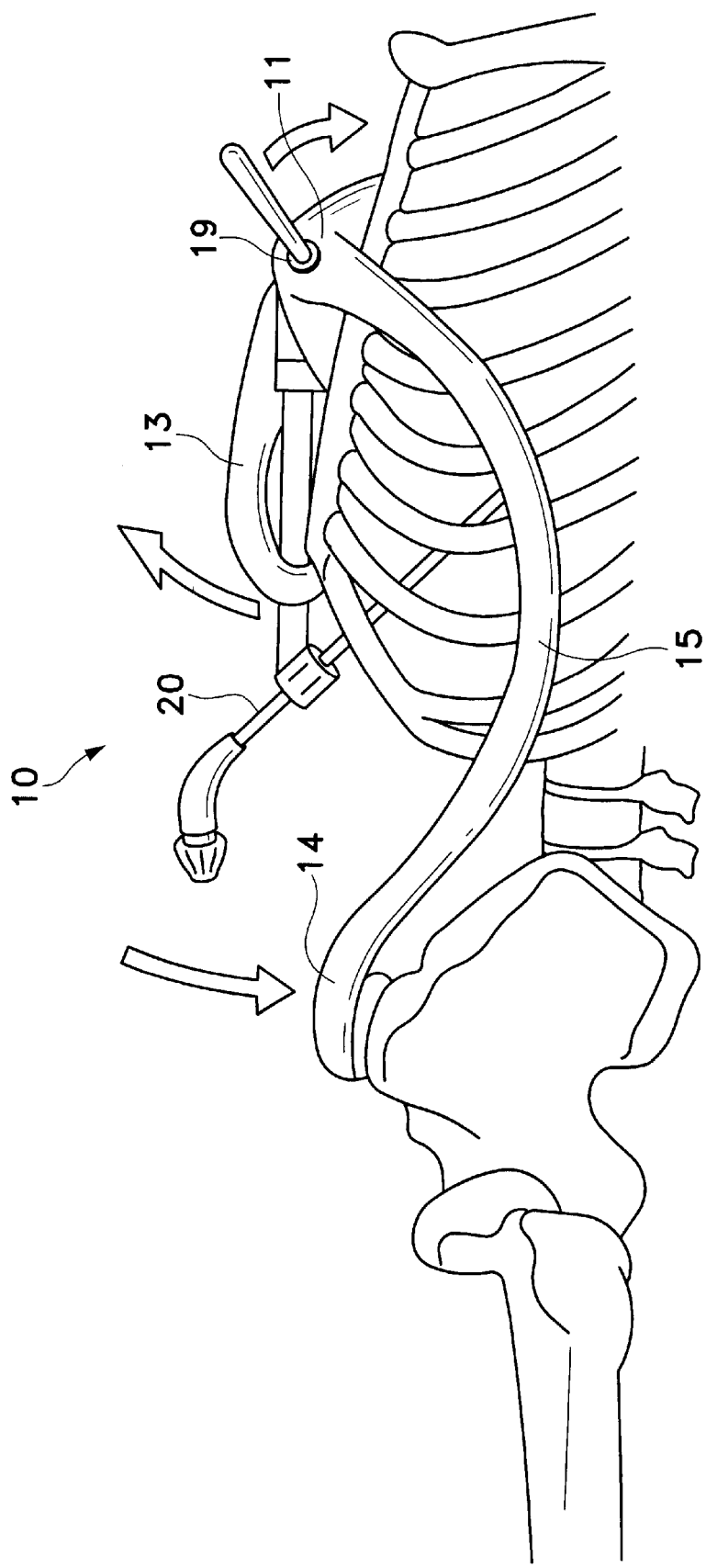
FIG. 5 is another embodiment of the offsetting retractor assembly having a different configuration for the support arms.

Referring now to FIG. 5, a side view of the embodiment of FIG. 4 is shown to illustrate a preferred configuration for the support arms 15. As can be seen in FIG. 5, the support arms 15 may be configured to contour to the side of the patient's thoracic cavity and to drop below the level of the xyphoid appendage and the lifting arm 13 to avoid obstructing the surgeon and the surgeon's access to the surgical field via the xyphoid access incision. As shown, the frame 11 is resting against approximately the midpoint of the center of the sternum, and the lifting arm 13 is engaging the bottom left portion of the sternum. A beating heart stabilizer 20 is affixed to the frame 11 and is entering the thoracic cavity to engage the beating heart via the xyphoid incision. At the distal end of the support arms 15, the retractor assembly braces 17 abut the pelvis for overall stability of the retractor assembly 10.

Figure 6A:
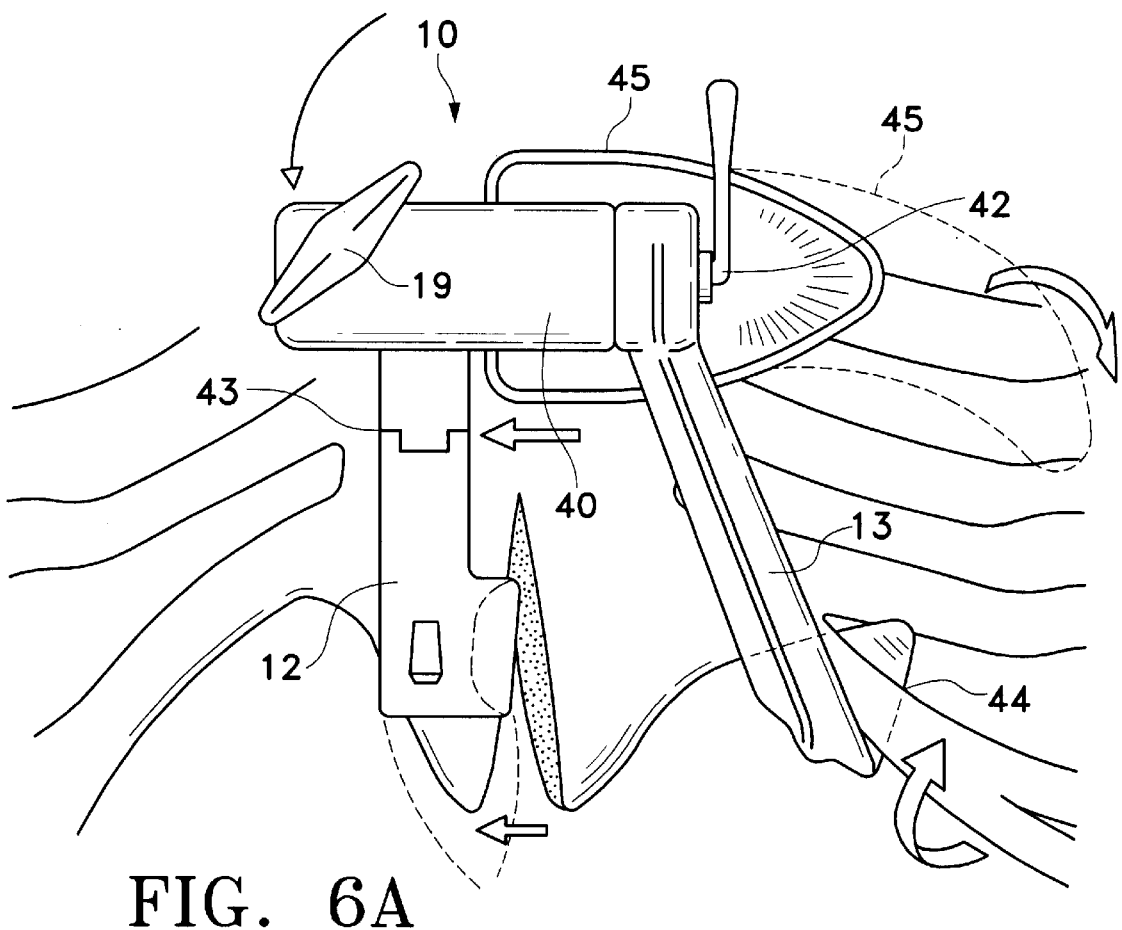
FIGS. 6A and 6B are another embodiment of a retractor of the invention without support arms.
Figure 6B:
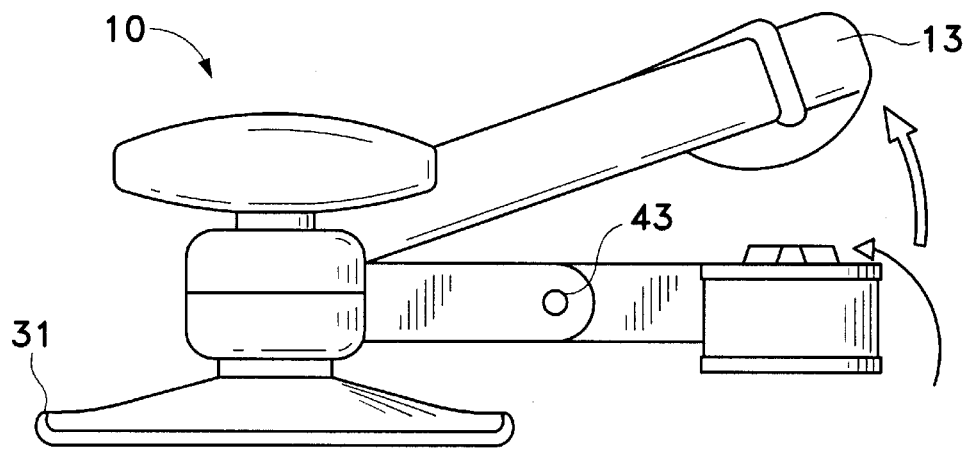

Referring to FIG. 6A, a retractor assembly 10 may be provided that is of a minimal size and still facilitates access to the beating heart via the xyphoid incision. In this embodiment, the retractor arm 12 is movable and has a lockable hinge 43 that pivots at a point in the retractor arm 12 that allows the distal blade 44 to be positioned advantageously to engage one-half of the edge of the incision that traverses the xyphoid appendage. The retractor arm 12 is actuated by the spreader member 19 that is configured to move retractor arm 12 relative to a housing 40 that contains the mechanism for moving retractor arm 12 relative to lifting arm 13. The retractor assembly 10 is further comprised of a support pad 45 that preferably extends from beneath housing 40 to cover and conform to the skin at least a portion of the thoracic cavity to provide sufficient support in stabilization to allow lifting arm 13 to be vertically offset while maintaining a stable surgical field via the xyphoid incision. As in the other embodiments described herein, the distal blade 44 at the end of lifting arm 13 engages the lowermost portion of the left side of the rib cage at the edge of the bottom most rib. A fixed position for the lifting arm 13 may be provided by a conventional ratchet (not shown) as described in FIG. 3 above, or may be comprised of a crank 42 or other mechanism to raise the position of the lifting arm 13 and to fix the position of the lifting arm 13 in place during the surgical procedure. Similarly to the other embodiments, a retractor assembly 10 of FIG. 6 may also have a fixture for mounting a beating heart stabilizer associated with the retractor arm 12, housing 40, or lifting arm 13 as needed to incorporate the beating heart stabilizer (not shown) into the retractor assembly 10. FIG. 6B is a side view of the embodiment of FIG. 6A showing a rotatable locking mechanism at the hinge 43 for positioning the retractor arm 12 to engage the incised xyphoid appendage relative to the retractor assembly 10. As can be seen in FIG. 6B, the lifting arm 13 is vertically offset to a position above the retractor arm 12 and access to the surgical site via the xyphoid incision is provided by the space created from the vertical offset of the lifting arm 13 relative to retractor arm 12.

Figure 7:
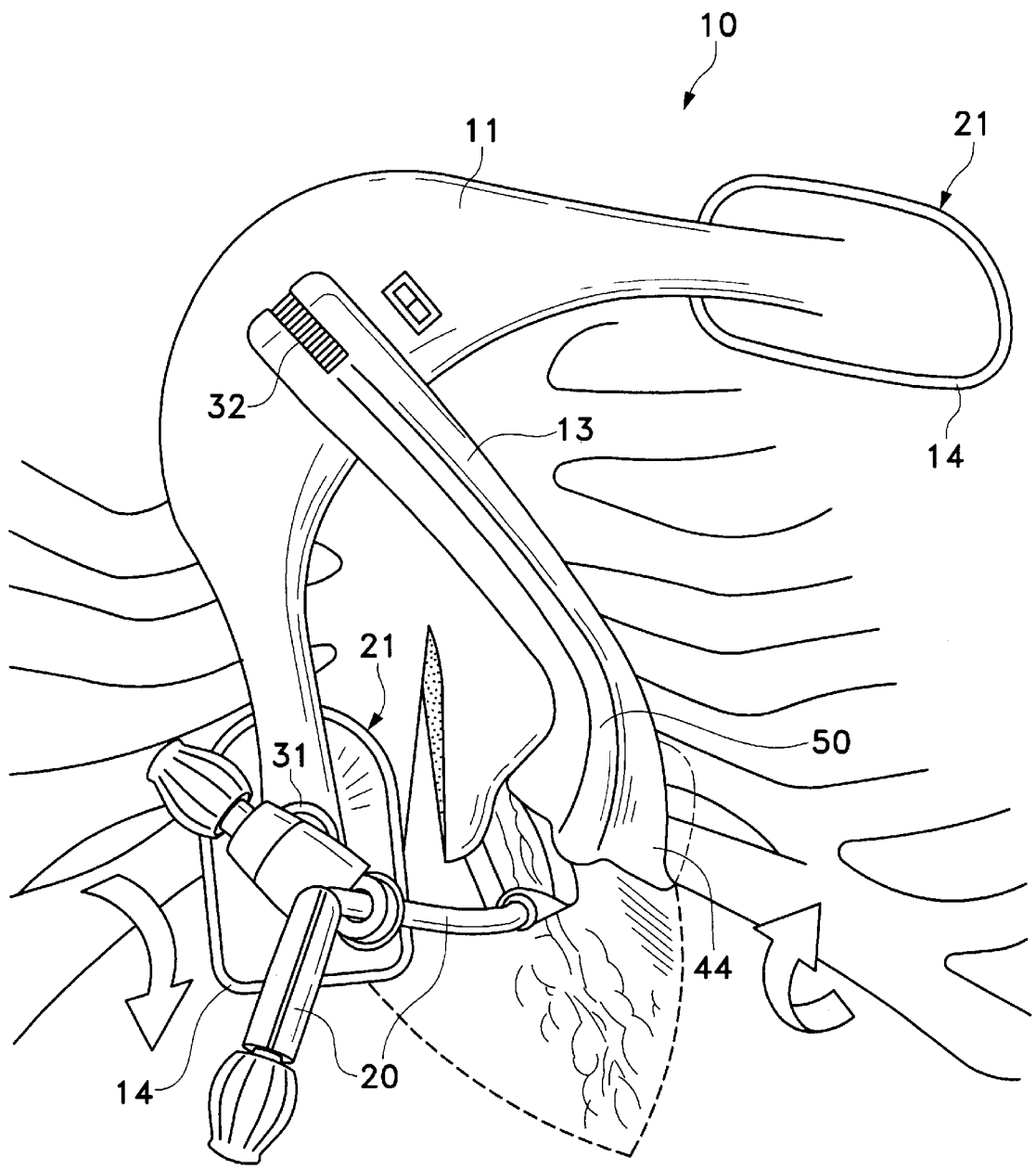
FIG. 7 is a further embodiment of the offsetting retractor of the invention having a single lifting arm and designed for asymmetrical positions relative to the medial line of the sternum.

Referring to FIG. 7, a further embodiment of the invention is comprised of a retractor having a single lifting arm 13 and configured for asymmetric positioning relative to the midline of the sternum of the patient. In the embodiment of FIG. 7, a lifting arm 13 is affixed to a frame 11, preferably at substantially a midpoint thereof such that the distal blade engages the lower left rib cage proximate to the xyphoid appendage. To achieve maximum leverage at the lower left sternum, a pair of contact points 21 with support pads 14 are placed proximate to the lower right rib cage proximate to the xyphoid appendage and to the upper left thoracic region. Elevation of lifting arm 13 may be achieved by conventional means such as the mechanical expedience described herein, or a lockable ratchet system as shown. As in the above embodiments, the distal end 44 of the lifting arm 13 lifts the left bottom rib proximate to the xyphoid appendage and is raised to provide access via the xyphoid incision. Also as in the other embodiments, a fixture 31 for attachment of a beating heart stabilizer 20 is provided at a convenient location of the retractor assembly 10 and a light (preferably fiber optic) is attached to the lifting arm 13 to illuminate the surgical field.

While the above description contains many specificities, these should not be construed as limitations on the scope of the invention, but as an exemplification of preferred embodiments thereof. Accordingly, the scope of the present invention is determined not by the embodiments illustrated herein, but by the appended claims and their legal equivalents.

We claim:

1. Surgical apparatus or accessing a beating heart via a xyphoid incision comprising:
   means for vertically offsetting a portion of the rib cage through an incision proximate to or through a xyphoid appendage without substantially transecting the sternum; and
   a beating-heart stabilizer.

2. The apparatus of claim 1 wherein the vertically offsetting means is a retractor having a lifting arm operably attached to a retractor frame.

3. The apparatus of claim 2 wherein the lifting arm has a locking mechanism to fix a position of the lifting arm in a vertically offset configuration.

4. The apparatus of claim 2 further comprising a retractor arm operably attached to the retractor frame.

5. The apparatus of claim 1 further comprising supporting arms attached to a retractor frame and having a plurality of contact points to engage a patient's body.

6. A method of performing cardiac surgery on a beating heart comprising:
   making an incision proximate to or through a xyphoid appendage without substantially transecting the sternum;

inserting an offsetting retractor into the incision;

vertically offsetting at least a portion of the rib cage using the retractor;

performing a cardiac surgical procedure.

7. The method of claim 6, further comprising introducing a beating-heart stabilizer into the incision to contact the beating heart.

8. The method of claim 7, wherein the beating-heart stabilizer exerts a mechanical force to stabilize the beating heart proximate to the site of a target coronary artery.

9. The method of claim 7 wherein the beating-heart stabilizer uses suction to attach to the beating heart.

10. The method of claim 6 further comprising:

introducing an organ positioner into the incision to engage an internal organ.

11. The method of claim 10 wherein the cardiac surgical procedure establishes a coronary artery bypass graft.

12. The method of claim 6 further comprising harvesting an internal mammary artery.

13. The method of claim 12 wherein the harvested internal mammary artery is used as a source artery for a coronary artery bypass graft.

* * * * *